United States Patent [19]

Semm

[11] Patent Number: 4,464,169
[45] Date of Patent: Aug. 7, 1984

[54] APPARATUS AND METHOD FOR INSUFFLATING FLUID MEDIA INTO A CAVITY

[76] Inventor: Kurt Semm, 4 Hegewischstrasse, D 2300 Kiel 1, Fed. Rep. of Germany

[21] Appl. No.: 311,515

[22] Filed: Oct. 15, 1981

[51] Int. Cl.³ .......................................... A61M 13/00
[52] U.S. Cl. ...................................................... 604/26
[58] Field of Search .......... 604/26; 128/748, DIG. 13

[56] References Cited

U.S. PATENT DOCUMENTS

| | | | |
|---|---|---|---|
| 3,870,072 | 3/1975 | Lindemann | 604/26 X |
| 3,982,533 | 9/1976 | Wiest | 604/26 |
| 4,048,992 | 9/1977 | Lindemann et al. | 604/26 |
| 4,207,887 | 6/1980 | Hildebrandt et al. | 604/26 |

FOREIGN PATENT DOCUMENTS 2803646  8/1979  Fed. Rep. of Germany ........ 604/26

*Primary Examiner*—Lee S. Cohen
*Attorney, Agent, or Firm*—Fleit, Jacobson, Cohn & Price

[57] ABSTRACT

The present invention relates to an apparatus and method for insufflating fluid media into a cavity of a human or animal body, particularly the abdonimal cavity. A single hollow needle is utilized for intermittently insufflating the gas into the body cavity. Thereafter the flow of gas is interrupted and then the needle is connected with a pressure measuring device to determine both the static and dynamic fluid pressure of the body cavity. The amount of fluid insufflated can also be measured with the aid of the same hollow needle. Using the needle for insufflating will insure that the measuring will be correct since the gas during insufflating will blow any blood clots and/or tissue into the body cavity. The conduit leading to the needle may be split in a number of branches to insufflate gas at desired different pressures and/or volumes which again are variable. Most of the operation can be effected automatically. A display panel giving a visual indication of the parameters can also be provided.

25 Claims, 4 Drawing Figures

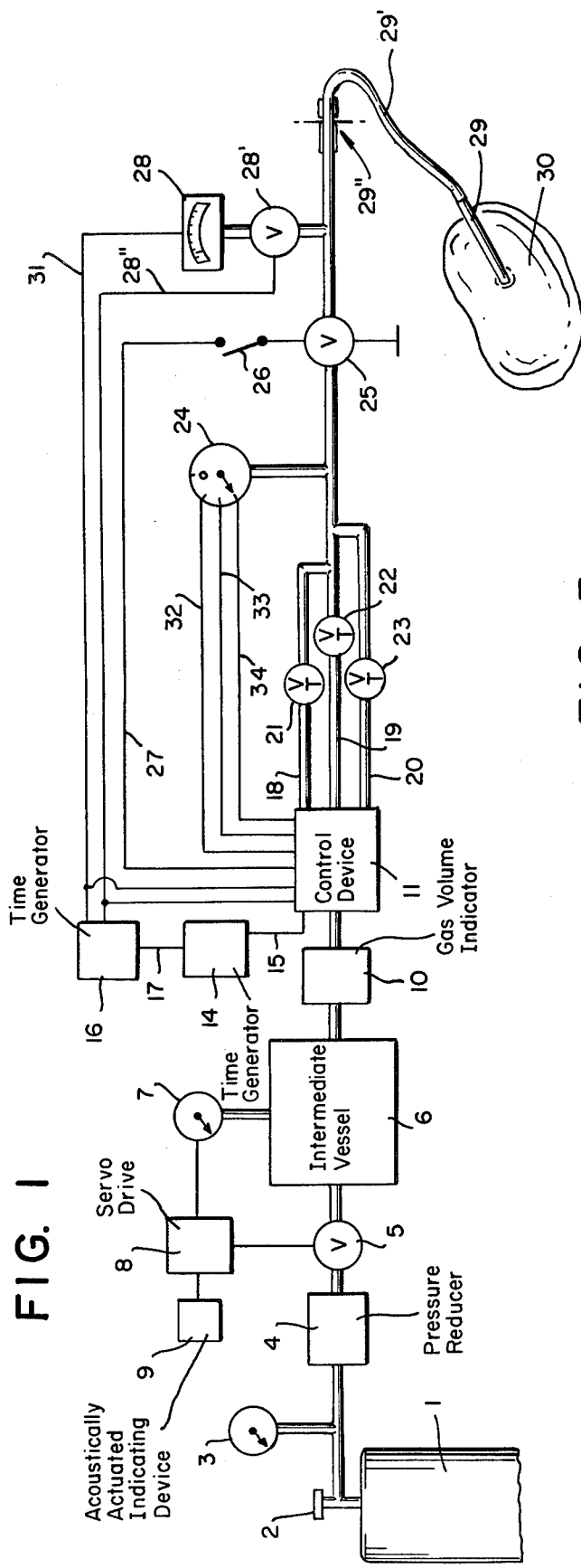
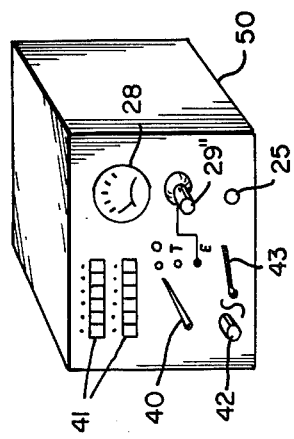
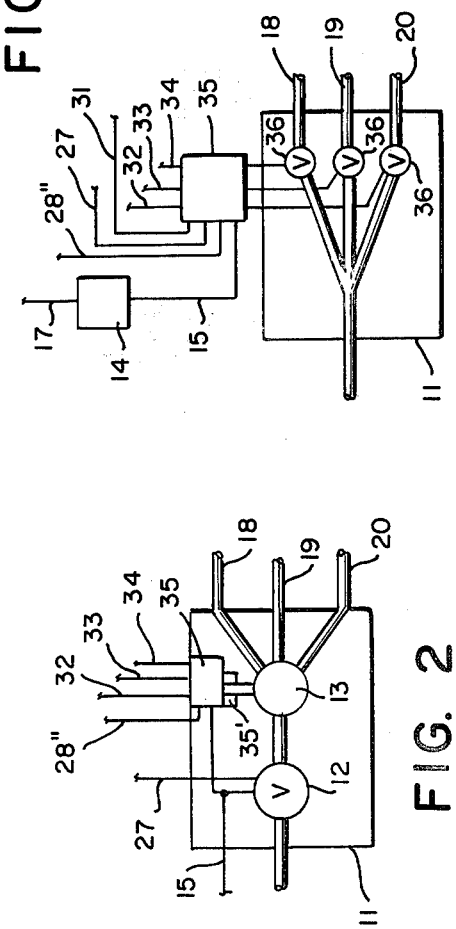
FIG. 1
FIG. 2
FIG. 3
FIG. 4

APPARATUS AND METHOD FOR INSUFFLATING FLUID MEDIA INTO A CAVITY

BACKGROUND OF THE INVENTION

The invention relates to an apparatus and method for insufflating fluid media, in particular $CO_2$ gas, into a cavity of a human or animal body, where the fluid flows from a source under pressure via a pressure reducer to an intermediate vessel and by which the fluid medium is conveyed via a line provided with a shut-off valve into the body cavity and in which a pressure measuring device is provided with which the body cavity pressure is measured.

German Gebrauchmuster No. 75/08556 proposes an insufflator for the introduction of limited amounts of carbon dioxide gas into the human body, where via a first line the gas is supplied to the human body while the pressure adjusting itself in the body is being measured via a second line. This document states that an instrument-side pressure adjustment which corresponds to the pressure desired in the human body cannot be fixed exactly because of the backpressure which builds up in the first line and in the Veress needle. To avoid these disadvantages, the first and second lines are connected either with a double-barrel Veress needle or with two single-barrel Veress needles. Both lines are connected on the instrument side, the pressure produced in the body cavity being connected on the instrument side, the pressure produced in the body cavity being measured via the second line, which communicates with a pressure gauge provided in the housing. Use of such Veress needles, however, has the disadvantage that the feed aperture for the gas and the measuring aperture at the double-barrel Veress needle or respectively at the two single-barrel Veress needles are not identical. It may happen, therefore, that the gas supply aperture is separated from the measuring aperture by a body membrane, the fed gas inflating a body cavity without the pressure gauge indicating this fact. This danger is especially great when two single-barrel needles are used. On the other hand, the measuring aperture of the needle may become clogged by blood or tissue parts, for example, so that again no pressure variation will become visible on the pressure gauge. Such faulty indication naturally represents an increased risk for the patient, if not a life threatening situation.

In German Auslegeschrift No. 25 44 567 a gas insufflator is described where via a first line and a cannula the gas is introduced into the body cavity. This cannula is double-barreled, that is, the cannula is surrounded by a tube which distally opens into the body cavity and proximally is connected to a contact manometer via a measuring line. At a certain pressure this contact manometer closes a contact by which a valve disposed in the feed line is closed and in addition an alarm device is actuated. As in the above mentioned Gebrauchmuster, the openings located in the body cavity for introducing the gas and for measuring the pressure are not identical, so that here, too, clogging of the measuring aperture may occur. Thus the above mentioned disadvantages again are present.

What the two known devices have in common is that they are to pick up the pressure in the body cavity more exactly via a return line, making it visible on a display. It is only in the Auslegeschrift that the infeed is closed when a certain limit pressure is exceeded. If this limit pressure drops, this valve will be reopened, so that gas moves up into the body cavity again. This procedure, which replaces the manual operation of the insufflator by an automatic regulation, suffers, as has been said, from the danger of clogging of the measuring aperture and from the different arrangement of the feed and measuring apertures.

It is the object of the invention to provide a device for insufflating fluid media into human or animal bodies where the measuring aperture is prevented from clogging safely and which permits reliable determination of the pressure in the body cavity and possibly also the automatic regulation of this pressure.

SUMMARY OF THE INVENTION

The present invention overcomes the difficulties encountered in the prior art arrangements by providing a single insufflation needle which alternately insufflates into a body cavity, particularly the abdominal cavity. Thereafter, the insufflation is stopped and the pressure conditions are determined. This changeover may be done automatically or by hand, that is, by opening and closing various valves. The insufflation needle becomes permanently connected with a vessel containing the fluid medium, particularly $CO_2$ and the various measuring devices. Here again the connection between the insufflation needle and the measuring devices is from time to time closed and opened. Closing and opening of the various valves may be effected by hand or automatically at predetermined time intervals, or on the basis of the data provided by the measuring devices.

One of the main advantages of a single insufflation needle resides in the fact that any blood clots or body tissue in the insufflation needle is automatically blown into the body cavity when fluid pressure is passed through the needle into the body cavity. The present invention also includes a method of insufflating gases into body cavities and intermittently measuring the pressure in the body cavity.

Advantageous developments will be evident from the sub-claims.

The invention eliminates the risk that the measuring aperture is inoperative because it is located in a wrong position or due to clogging with tissue parts. In the device according to the invention, in fact, the feed aperture in the body cavity and the measuring aperture are identical, i.e., during the introduction of gas into the body cavity the needle or cannula tip is the feed aperture, while in the measuring stage it is utilized as measuring aperture. On the instrument side this requires, of course, an interruption of the feed line by a valve which is provided in a control device and is actuated at certain intervals of time. By this intermittent mode of operation it is possible to combine the feed aperture and the measuring aperture at one measuring point, so that wrong indication of the pressure due to local separation of these apertures will no longer occur. Also obstruction of the measuring aperture by vessel parts is prevented, as the aperture is immediately blown free after switching to gas feed, and clogging is prevented by the intermittent mode of operation.

This mode of operation further requires only one simple single-barrel cannula and only one feed line, so that the use of complicated double-barrel cannulas and of several lines is obviated. In addition, with only one needle being introduced into the body, any introduction of an additional needle becomes superfluous, this being of importance both for the patient and for the gas proofness of the body cavity.

The gas pressure measurement and the limitation of the gas pressure is effected in the device according to the invention with a contact manometer which is disposed in the line between the control device and the cannula. This contact manometer can be set to a certain pre-selected limit pressure at which the valve provided in the control device for shutting off the gas supply are reliably closed. If several lines, over which gas is passed at different pressures and rates of flow, branch off from the control device, the contact manometer may be equipped advantageously with additional contacts. These contacts, which are set to a certain pressure in the body cavity, can successively activate valves in the gas supply phase, i.e., with the control device open. In the initial stage, i.e., at a very low body cavity pressure one activates the valve through which relatively small quantities, so that, e.g., 1 liter/min of gas at a pressure up to 6.6 kPa, can be supplied to the body cavity. Due to the intermittent mode of operation, the pressure actually prevailing in the body cavity is continuously measured at the contact manometer and compared with the contacts. If in the measuring phase the indicator comes in contact with a further contact, switching to a second valve occurs, through which, for example, 1 ltr/min gas is supplied to the body cavity at about 1.6 to 2.6 kPa. This procedure can be continued with any desired number of contacts, the last contact setting in operating a valve in such a way that it gives off the gas under a still lower pressure, for example, about 1–2 kPa, in a quantity of about 1–3 ltr/min via the cannula into the body cavity.

In a further embodiment of the invention, only a valve is provided in the control device which upon execution opens or closes the line. Downstream, behind this valve, a cock is provided which is controllable, either manually from the front panel or automatically through a servo device. In the same manner as explained above, this cock can be connected successively with lines which supply the gas to be fed to the body cavity at different pressures and rates of feed. The manual activation of the cock is effected by regular reading of the contact manometer and routine adjustment to the desired gas feed value. In this embodiment the contact manometer has only one contact which fixes the pressure limit in the body cavity and closes the valve provided in the control device when this pressure is reached. If a servo drive for the cock is provided, the contact manometer may comprise additional contacts, through which, via the servo device and the control device, the cock is brought into the desired position.

Furthermore, instead of this analog contact manometer a digital contact manometer may be used, in which the limit pressure value, as well as the pressure values for operation of the individual valves, can be entered digitally. Further, this digital pressure measuring device can, independently of whether it is used for gas regulation, digitally store the pressure value reached in the measuring phase, until renewed measurement in the measuring phase, which may be the case optically and/or by printout. This indication ensures a reliable mode of operation, as the last pressure value measured in the body cavity can always be ascertained.

The control generator is switched on and off via a first time generator whose running time corresponds to the gas feed phase and can be pre-selected at will. Upon start of the time generator, the respective shut-off valves are opened through the switching on of the control generator, so that the gas can flow downstream to the body cavity. When the time set on the first time generator has expired, the control generator is actuated, whereby all valves in the control generator are closed. Simultaneously a second time generator starts up, whose running time is likewise adjustable and which serves to set the measuring time. Within this measuring time, the pressure prevailing in the body cavity can be reliably measured and via the contacts present in the contact manometer the respective valves fixed in the control device. When the second time generator has run through the pre-selected time, which is normally put in as a fixed constant, it again switches on the first time generator, the gas feed mechanism proceeding anew. The time phase of the first time generator is advantageously selected so that it is relatively greater than for the interruption phase.

Furthermore, this monofil safety system can be used for the purpose that when a life-endangering intracorporal overpressure is exceeded, a safety valve automatically lets off the overpressure and closes the valve provided in the control device.

In accordance with the present invention, escaped or absorbed gas is quickly replaced by use of overpressure to a pre-selected maximum pressure level. Here only a measured quantity is insufflated into the body cavity which in its turn never creates a dangerous intracorporal pressure increase. It is only the multiple replacement of this measured quantity that leads into the limit ranges, which are always sampled by intermittent monofil pressure measurement. By this intermittent, monofil insufflation technique the following advantages for the patient are achieved:

In manual actuation of the cock the physician operates only a single-lever apparatus and thereby decides on different gas quantities to be supplied.

The gas outlet from the cannula is identical with the inlet apertures for the measuring line, leading to correct test results.

A second measuring hose for static pressure indication is obviated.

Via the monofil system dangerous overpressure can always be let off from the body cavity.

Also in endoscopic surgery, i.e., at unexpectedly high gas loss, the operator always has available an optimally replenished intracorporal gas bladder, which is physiologically acceptable, for continuing his operation without the expense of additional personnel.

BRIEF DESCRIPTION OF THE DRAWING

FIG. 1 is a schematic block diagram illustrating the most important components, and embodiment, of the invention;

FIG. 2 is a plan view of the manual and automatic control device incorporated in FIG. 1;

FIG. 3 is a control device of another embodiment;

FIG. 4 is a perspective view of a cabinet containing the control device.

DESCRIPTION OF THE PREFERRED EMBODIMENTS

According to FIG. 1, a compressed gas vessel 1, containing for example $CO_2$ gas, laughing gas, or oxygen, is provided as compressed gas source for the availability of the gas to be introduced into the body cavity. This compressed gas vessel 1 is opened by means of a hand valve 2, the issuing gas being passed via a pressure gauge 3 to a pressure reducer 4. In this pressure reducer the gas under high pressure is expanded to an operating pressure of about 300-400 kPa, while the manometer 3 indicates the level in vessel 1. The low-pressure gas flows via a valve into an intermediate vessel 6, the volume content of which can be read on the manometer 7. The volume of the intermediate vessel is preferably rated so that the gas quantity fed in the intermediate vessel is sufficient for a single filling of a body cavity without creating a critical pressure state in the body cavity.

If, however, larger gas quantities must be introduced into the body cavity, for example due to gas loss at leakage points, the intermediate vessel 6 can either be filled again by manual operation of valve 5. Or this filling can proceed automatically, if the manometer 7 comprises a contact which opens valve 5 via a servo drive 8. The servo drive 8 comprises an indicating device 9 which indicates acoustically and/or optically the start of filling and the number of fillings. After the filling of the intermediate vessel 6, valve 5 closes again automatically.

To record the total gas consumption during the insufflation, following the intermediate vessel 6 a gas volume indicator 10 is provided which by means of a gas volume meter the exact gas volume consumed.

Following this gas volume indicator 10 is a control device 11, by which the entire subsequent gas supply path can be closed or opened in suitable manner.

The first embodiment, details of which are shown in FIG. 2, this control device 11 comprises firstly a valve 12, which, controlled either manually or electronically, being designed as a solenoid valve, can be closed and opened. In the open state, the gas passes through by valve 12, flows via a cock 13 to one of the three branch lines 18, 19 or 20 selected by actuation of the cock. This cock 13, designed as hand lever from the front of the apparatus, can likewise be actuated by manual or electronic control. The branch lines comprise throttles 21, 22, and 23, which limit the flow of gas and the gas pressure. For example, the first throttle can limit the pressure to a maximum of 6.6 kPa and the flow to 1 ltr/min; the second throttle the pressure to about 1.6 to 2 kPa, and the flow to 1 ltr/min; and the third throttle the flow to 2-3 ltr/min. In the preferred embodiment, the first throttle limits the flow to 1 ltr/min, the second throttle to 2 ltr/min, and the third throttle to 3 ltr/min.

At the beginning of the insufflation, the branch line with the throttle which lets through the least gas flow quantity is selected. By such a selection a safe insufflation of the body cavity is ensured. When a certain pressure in the body cavity is reached, one can switch selectively to higher insufflation quantities, i.e., for example to 2 or 3 ltr/min. When the desired pressure is reached, the gas quantity consumed by absorption can be replenished by the highest flow step if needed.

The branch lines 18, 19 and 20, which behind the throttles 21, 22 and 23 are brought together again in one line, are followed by a pressure measuring device as, e.g., a contact manometer 24, by which at least a threshold value or the end pressure can be set (via a contact).

After passing through the contact manometer 24, the flowing gas advantageously passes through the valve 25, which is adjusted to the maximum pressure level of the respective body cavity. This valve 25 opens automatically when this maximum pressure level, for example 4 kPa, is reached and exceeded. Simultaneously, a contact 26 closes, which, via the line 27, sends a signal to valve 12, whereupon the latter is closed.

This valve 25 is followed by a pressure indicating device 28 and then by the needle 29 introduced into the body cavity 30, which needle is advantageously designed as a single-barrel Veress needle. The pressure indicator 28 stores in digital or analog form the last body cavity pressure measured in the measuring process and reproduces it optically as reference function until the next process.

The apparatus according to the invention is operated as follows:

As the gas introduction aperture and the measuring aperture at the tip of the needle are identical, the device according to the invention is switched alternately, that is, intermittently, to gas conduction or measuring. This is achieved in that a time generator 14 starts up, which is connected via line 15 with the control device 11, and in particular with valve 12. This time, generator 14 controls the gas feed time, that is, the time during which valve 12 is open. The signal transmitted from this time generator 14 to the control device 11 can either turn on a logic switch 35, which in turn actuates valve 12, or can actuate valve 12 directly. The time during which the time generator 14 keeps valve 12 open is pre-selectable at will on the time generator and can be selected from a few seconds to minutes. When this open time is passed, the time generator 14 sends the closing signal to the control device 11 or respectively valve 12, whereupon the gas supply path is closed. At the same time, an opening signal is passed from time generator 14 via line 17 to time generator 16, which establishes the measuring time. This time generator 16 is connected, for example, to the pressure indicator 28 via line 31 and switches it on at the beginning of the measuring phase and off again at the end. This pressure indicator 28 stores the last pressure value of the body cavity measured during the measuring phase. The measuring time of the entire apparatus is to be rated so that it is sufficient for an exact pressure measurement. It has been found that measuring times for measuring the static pressure within the line lie in the range of at most a few seconds, normally a measuring time of 0.2-1.5 seconds being chosen. Within this measuring time, the pressure value indicated on the contact manometer 24 becomes stabilized, and the indicator may be able to close the contact which is operable only during the measuring phase. If the set pressure limit is exceeded, the signal generated by the closing of the contact can cause closure of valve 12 via line 27.

Advantageously, the contact manometer 24 comprises several contacts, each connected via the lines 32, 33, 34 with a servo drive 35' which can connect the cock 13 with one of the branch lines 18, 19 or 20. By the closing of one of the contacts, therefore, a specific flow path through a specific branch line is selected during the measuring phase with the aid of the servo drive 35'. The setting of the contacts is selected so that at the beginning of the insufflation, for reasons of safety, only a maximum of 1 ltr/min gas flows at maximum 6.6 kPa. Only when the pneumoperitoneum is almost perfect, one switches to another branch line. With such a circuit arrangement a complete, automatically performed insufflation of the body cavity is achieved, so that the physician need not pay any particular attention to it any more after the apparatus according to the invention has been turned on.

The pressure measuring device designed as contact manometer 24 may, of course, be either analog or digital; instead of settable contacts of the manometer, the preselected limit values are then fed or placed in memory in settable or read-in pressure measuring sensors as constants.

When in the second time member 16 the time set as measuring time has expired, it switches the first time member 14 on again via line 17 and, at the same time, via line 28" a measurement attenuation valve 28' before the manometer 28 is set in closing position. The measurement attenuation valve 28' therefore is operated in opposition to the insufflation phase and in synchronism with the measuring phase, so that continuous reading is possible on manometer 28 and the intermittent operating pressure does not disturb the reading on manometer 28. During the gas supply phase, the flow pressure is picked up by the pressure measuring device 24 or respectively by its pressure measuring sensor. Each pressure measuring sensor has at least one settable threshold value which, depending on design, can be entered in analog or digital form and sends its signal to the logic circuit 35 via lines 32 to 34.

The logic circuit 35 is essentially constructed so that the branch lines 18 to 20 can convey the fluid medium to the cannula 29 in automatic insufflation as needed. This means that a priority circuit must be provided which permits the activation via logic gates of only one branch line 18 to 20. If, therefore, for example, a branch line which carries 2 ltr/min of the fluid medium is to be taken into operation, then the logic circuit 35 must activate the servo drive 35' for operation of cock 13 until cock 13 opens the respective line.

In FIG. 3, another embodiment of the invention is shown, where the gas line coming from the gas volume indicator 10 branches into the branch lines 18 to 20 and each of these branch lines has at the entrance a control valve 36 which is closed without control energy and which is preferably designed as a solenoid valve. The control valves 36 are actuated by the logic circuit 35 in a similar manner as the servo drive 35' for cock 13 in the form of realization according to FIG. 2.

Accordingly, the logic circuit 35 has the function not only of a priority circuit for the activation of only one branch line 18 to 20, but also of opening of the control valve 12. According to FIG. 3, the operation of control valves 36 is made possible only when contact 26 of the safety valve 25 does not already signal the reaching of a maximum pressure. Such safety signals, as are signaled for example also by the pressure measuring device 24 when, for example, the highest set pressure is being exceeded, can reliably prevent wrong operation of a valve via a logic AND circuit. Naturally also the signals emitted by the two time members 14 and 16 are fed into the logic circuit 35. Essential for the logic circuit is moreover that the prevailing pressure conditions are stored by the pressure measuring device 24 and/or the manometer 28 and compared with the actual pressure, because it can thereby be determined for example whether the main insufflation process is completed, and automatically a switching to another branch line is made possible, with which only the medium escaping in the body cavity or in the line path is replaced. When, therefore, the stored pressure conditions and the quantity conditions supplied for example by the gas volume indicator 10 are processed in the logic circuit 35, it results that the consumed quantity of fluid medium is very small in the existing time intervals. But if the pressure measuring device 24 or the manometer 28 reports that the pressure suddenly drops, the sudden pressure drop will be built up again by a rapid insufflation due to the action of the logic circuit. Hence the branch lines provided for rapid insufflation are switched on, and then, either automatically or by release for example with a foot switch by the operator, rapid insufflation can be actuated and thereby the original conditions can be restored. If a rapid insufflation has been triggered, this may lead to a further signal command triggering a renewed filling of the intermediate vessel 6.

All these signals and commands as well as logic control processes and set and actual test data can optically signalize the happening to the operator via optical indications and alarm indications.

According to FIG. 4, however, thrifty instrumentation and operation of the cabinet surrounding the apparatus according to the invention is provided to the extent possible, so as not to confuse the operator in a stress situation by too many control elements and lights. In a preferred embodiment on one side of the cabinet, only the minimum instrumentation and actuating devices are provided, while on another side, not shown, all control lamps are provided which may be located in the field of vision of a nurse who then can inform the operator of any disturbance, without thereby interfering with the operation itself.

On the front panel in the embodiment according to FIG. 4 is provided at least the main terminal, i.e., the monofil terminal 29", which leads to the insufflation needle 29 and through which the intermittent mode is maintained and carried out. In the surrounding field of this terminal is disposed expediently the drain opening for an emergency valve 25, and the measuring device indicating the actual intra-abdominal pressures, for example, the manometer 28. As further terminals, only a main switch 40 is required which in the zero positions may turn off completely the apparatus, permitting a test mode in position P, and in position E allows the automatic insufflation mode to proceed. A digital display and data input device 41 is conveniently arranged on the front panel of the cabinet 50. Via this digital data input and display device, both the static and the dynamic pressure for the respective desired pressure conditions, when one of the branch lines 18 and 20 is switched on, can be selected and read.

In addition to the main switch, a terminal for a foot switch 42 and a hand switch 43 is provided with which the rapid insufflation S can be activated if an apparatus is chosen wherein rapid insufflation is not carried out automatically via the logic circuit 35.

Other circuit configurations and setups can be chosen, as e.g., the arrangement of the valves 36 according to FIG. 3 behind the throttles 21 to 23, without the inventive idea in the present invention being thereby essentially modified. Valve 12, or a corresponding valve, may be designed as an analog valve, which, according to the measured potential pressure difference between insufflation pressure and static pressure, controls the volume of gas moving up per unit time. An analog valve would permit a continuous rather than an intermittent adaptation to the respective gas quantity requirements, thereby further refining an automatic operation.

In a further embodiment, switch 40 is replaced by a switch 40', which exhibits, instead of the adjustments O, T and E, the adjustments 0, 1, 2 and 3 ltr/min, the adjustment 3 ltr/min, replacing switch 43, because an insufflation with 3 ltr/min would correspond to the rapid insufflation releasable by switch 43. Thus, in a further embodiment, the entire apparatus is provided with only one switch to the position OFF or to the respective liter quantity per minute.

What constitutes insufflation pressure is not a constant figure, but a variable one. An additional switch may be provided in a further embodiment for the selectively maximum setting of the insufflation pressure for the production of the gas bladder, with the possibility of pre-selecting pressures of between 0.6 and 2 kPa. Further, it is necessary that as a function of the abdominal wall thickness of a patient and his depth of anesthesia, the pressure set to about 1.6 to 1.9 kPa be mechanically regulated so as to be variable. As this additional optional adjustment is not changed very often, the switch provided for it is preferably arranged not in the main control field, but at another point of the cabinet. In the region of the main switch for the adjustment of the flow from 0 to 3 ltr/min in continuous or intermittent adjustment, the front panel may, however, contain an additional switch for adjusting the gas bladder filling pressure in the stated range from 0.6 to 2 kPa. Thus, any operator and in particular the physician has the possibility, if the abdominal walls are very slack as is the case, e.g., with sterilization in the puerperium, to deviate from the previous 1.6 to 1.9 kPa and hence the possibility to go below the relatively still high pressures, which may lead to an overdistension of the abdomen. He can adjust to a physiologic range of 0.9 to 1.3 kPa. Essentially, however, pressure conditions around 1.6 kPa are dominant, which only rarely need to be varied upward or downward.

In a further advantageous embodiment of the invention, where the valve 25 is not necessarily provided on the front panel, the opening of the valve 25 may be connected with an alarm function, especially the combination with a whistle tone being preferred, as this whistle tone can be produced purely mechanically by a whistle. This whistle tone could sound, for example, when the male or female patient would start to press due to disturbances in the anesthesia or for other reasons and the respective emergency valve opens. Such an emergency whistle valve, e.g., in the form of a trill whistle, may also work in shunt, so that the free and rapid outflow of the gas is not hindered by the whistle.

In a still further embodiment, the connection of a foot switch may be provided, if at all, in the form of an override option, i.e., by actuation of such an external switch one intervenes in the automation only to the extent that a correction of the automation occurs only during actuation of this switch, and return to automatic operation, when the above switch is deactivated.

Different forms of flow meter can be incorporated in the logic circuit 35.

To summarize, it can be noted that the present invention for the first time makes possible an insufflation into a body cavity with an insufflation needle by which simultaneously the actual dynamic and/or static body cavity pressure can be measured. This is made possible essentially by an intermittent mode of operation, the intermittent operation and the respective prevailing pressure conditions even permitting an automatic operation be it under different operating conditions via a corresponding logic and memory circuit.

What I desire to protect by Letters Patent of the United States is not limited to the exemplary embodiments illustrated and/or described herein, but instead what is outlined in the appended claims.

I claim:

1. A device for insufflating fluid media such as $CO_2$ gas into a cavity of a human or animal body comprising;
   a vessel containing a pressurized fluid medium;
   measuring means for measuring the pressure of said medium in said cavity;
   a hollow needle having an aperture for insufflating said fluid medium into said cavity;
   an interruptible first conduit means having one end connected to said vessel and the other end connected to said needle for conducting said fluid medium from said vessel to said needle;
   an interruptible pressure measuring second conduit means having one end connected to said measuring means and the other end connected to said needle; and
   valve means connected with said first and second conduit means for alternately interrupting said first and second conduit means to alternately permit flow of said pressurized fluid medium to said hollow needle and to said measuring means respectively through the aperture in the hollow needle.

2. A device for insufflating fluid media into a cavity as claimed in claim 1, wherein said first conduit means comprises a number of branch lines; and adjusting means for each brach line to allow each branch line to transmit fluid medium at a different pressure.

3. A device for insufflating fluid media into a cavity according to claim 2, further comprising
   a pressure measuring device connected to at least one of said branch lines;
   a pressure control means for setting a threshold value for said branch line; and
   a signalling means connected to said pressure control means for indicating the reaching of said threshold value.

4. A device for insufflating fluid media into a cavity as claimed in claim 3, comprising
   a logic circuit connected to said pressure control means and said measuring means for transmitting signals to said control means.

5. A device for insufflating fluid media into a cavity as claimed in claim 4, comprising
   a timing device and a conduit between said logic circuit and said timing device for transmitting signals from said timing device to said logic circuit.

6. A device for insufflating fluid media into a cavity as claimed in claim 3, further comprising;
   means for adjusting said threshold value.

7. A device for insufflating fluid media into a cavity as claimed in claim 3, comprising
   a safety valve in said branch line for automatically opening upon said threshold pressure being reached.

8. A device for insufflating fluid media into a cavity as claimed in claim 1, wherein said first conduit means comprises a number of branch lines; and adjusting means for each branch line to allow each branch line to transmit fluid medium at a different flow rate.

9. A device for insufflating fluid media into a cavity as claimed in claim 1, comprising;
   a shut-off valve contained in said first conduit means for opening and closing said first conduit means;
   control means for setting a threshold pressure value for said shut-off valve; and
   shut off means for actuating said shut-off valve upon the pressure limit in said threshold value being exceeded.

10. A device for insufflating fluid media into a cavity as claimed in claim 9, wherein said shut-off means are operative automatically.

11. A device for insufflating fluid media into a cavity as claimed in claim 1, further comprising;
means for measuring pressures of carbon dioxide during operation of the apparatus and recording means for recording total gas consumption of said insufflating device; and
means for transmitting said total gas consumption to said recording means.

12. A device for insufflating fluid media into a cavity as claimed in claim 11, comprising
a box-type cabinet having a front panel;
visible display means on said front panel for visibly indicating the measurements recorded by said device.

13. A device for insufflating fluid media into a cavity as claimed in claim 12,
wherein said display means are calibrated.

14. A device for insufflating fluid media into a cavity as claimed in claim 1, further comprising;
control valve means for controlling the flow of said pressurized fluid medium to said needle and
an adjustable timing means for said control valve means for automatically controlling the cycles of said control valve means.

15. A device for insufflating fluid media into a cavity as claimed in claim 1,
wherein said measuring means is in the form of a manometer.

16. A device for insufflating fluid media into a cavity as claimed in claim 1, further comprising;
a static pressure measuring device connected to said first conduit means for measuring the pressure in said first conduit means upon interruption of said fluid flow.

17. A device for insufflating fluid media into a cavity as claimed in claim 1, further comprising;
a flow meter connected to said first conduit means for indicating the volume of the gas flow during the insufflating operation.

18. A method for insufflating fluid media such as $CO_2$ gas into a cavity of a human or animal body, comprising the steps of;
filling a vessel with a pressurized fluid medium;
measuring the pressure of said fluid medium in said vessel;
connecting a hollow needle having an aperture for intermittently insufflating said fluid medium from said vessel into said cavity;
intermittently measuring the pressure in said cavity; and
alternately insufflating that fluid medium into said cavity and measuring the pressure in said cavity using the same aperture in the hollow needle.

19. A method for insufflating fluid media as claimed in claim 18, comprising the step of
varying the pressure of said medium during said insufflating steps.

20. A method for insufflating fluid media as claimed in claim 18, comprising the step of
controlling said insufflating pressure so as not to exceed a threshold value.

21. A method for insufflating fluid media as claimed in claim 19, comprising the step of;
recording the measurements of said fluid media pressure of the insufflation during the operation.

22. A method for insufflating fluid media as claimed in claim 19, comprising the steps of;
recording; and
visibly displaying the measurements of the said fluid media pressure during the operation.

23. A method for insufflating fluid media as claimed in claim 18, comprising the step of
measuring the volume of said medium insufflated.

24. A method for insufflating fluid media as claimed in claim 18, comprising the step of
terminating the operation upon occurrence of an unsafe condition.

25. A method for insufflating fluid media as claimed in claim 18, comprising the step of
measuring the difference between the insufflating pressure and the static pressure in said cavity.

* * * * *